United States Patent [19]

Haaga

[11] Patent Number: 5,394,887
[45] Date of Patent: Mar. 7, 1995

[54] BIOPSY NEEDLE

[76] Inventor: John R. Haaga, 4309 N. Hilltop, Chagrin Falls, Ohio 44022

[21] Appl. No.: 180,972

[22] Filed: Jan. 14, 1994

[51] Int. Cl.⁶ .............................................. A61B 10/00
[52] U.S. Cl. .................................... 128/754; 128/749; 606/167
[58] Field of Search .............. 128/740, 751, 754, 752, 128/753, 757; 606/167, 170, 171

[56] References Cited

U.S. PATENT DOCUMENTS

| | | | |
|---|---|---|---|
| 3,477,423 | 11/1969 | Griffith . | |
| 4,340,066 | 7/1982 | Shah | 128/749 |
| 4,600,014 | 7/1986 | Beraha | 128/754 |
| 4,702,261 | 10/1987 | Cornell et al. | 128/754 |
| 4,735,215 | 4/1988 | Goto et al. | 128/754 |
| 4,953,558 | 9/1990 | Akerfeldt | 128/754 X |
| 5,273,051 | 12/1993 | Wilk | 128/753 X |

FOREIGN PATENT DOCUMENTS

| | | | |
|---|---|---|---|
| 728852 | 5/1980 | U.S.S.R. | 128/753 |
| 82/01988 | 6/1982 | WIPO | 128/753 |

*Primary Examiner*—Sam Rimell
*Attorney, Agent, or Firm*—Vickers, Daniels & Young

[57] ABSTRACT

A stylet for a biopsy needle is provided with a specimen recess inwardly of the distal end thereof which has a bottom wall parallel to the axis of the stylet and distal and proximal end walls which are reentrant relative to the distal end and proximal position of the stylet, respectively.

25 Claims, 3 Drawing Sheets

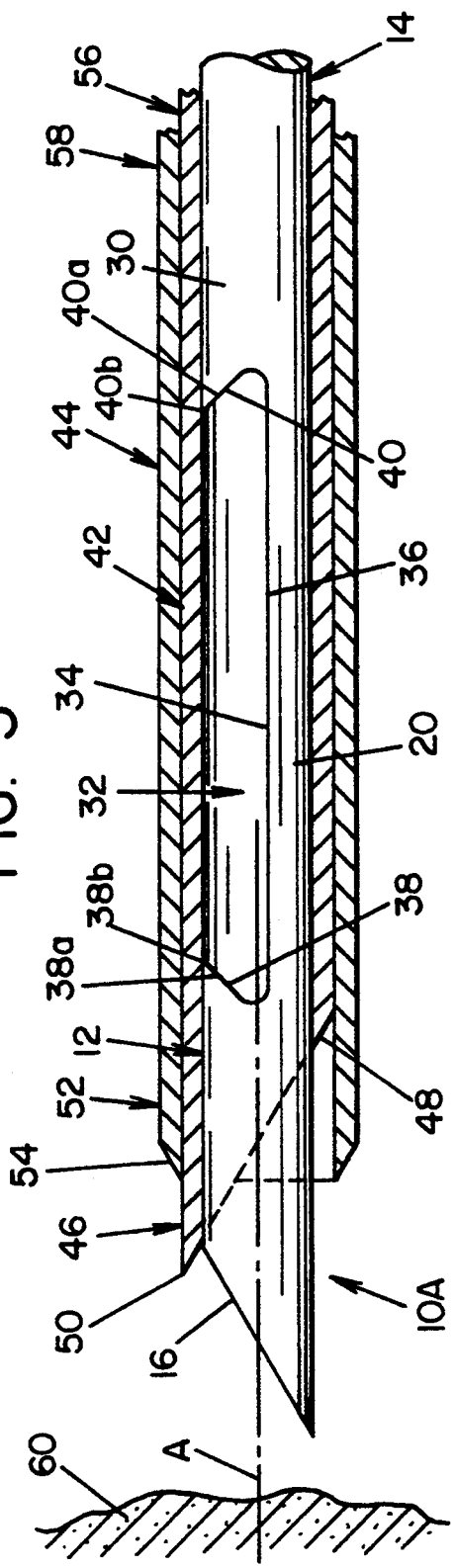
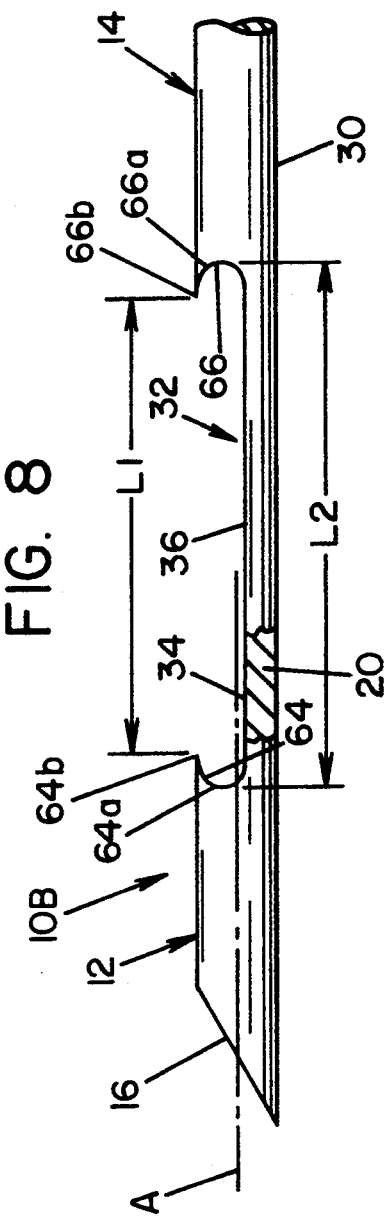

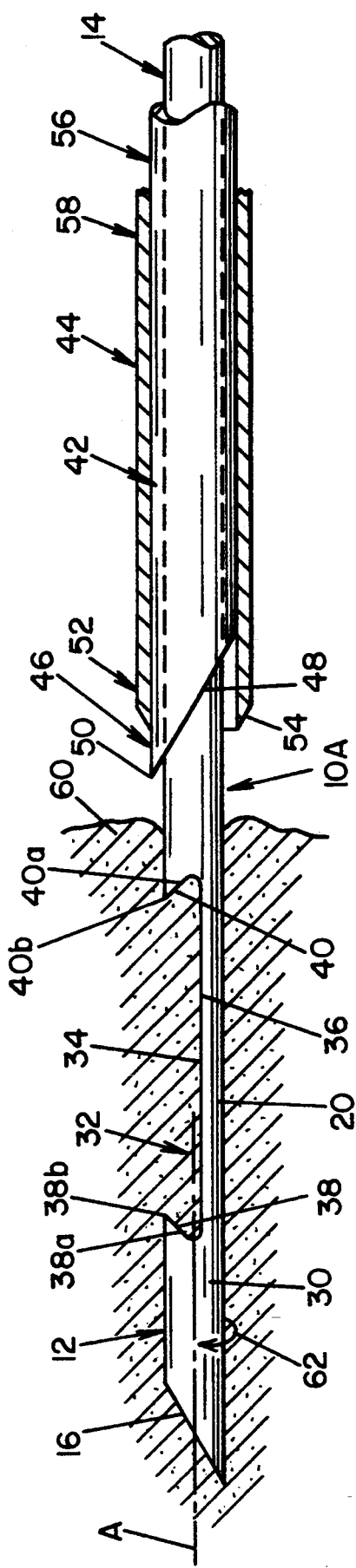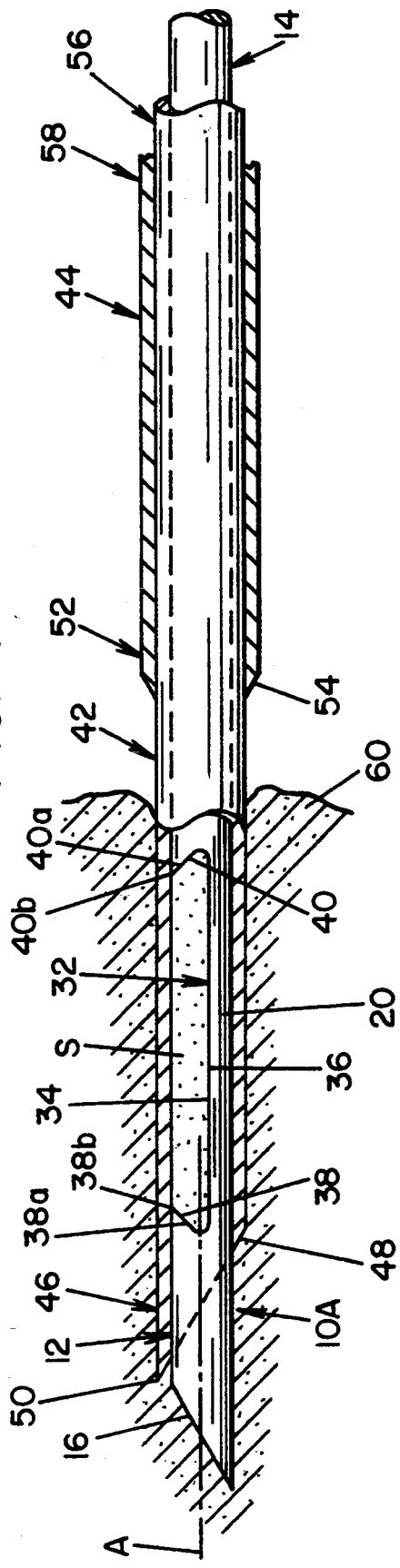

BIOPSY NEEDLE

BACKGROUND OF THE INVENTION

This invention relates in general to surgical needles and, more particularly, to improvements in a biopsy needle and a biopsy needle stylet which optimize cutting and withdrawal of tissue specimens during a biopsy procedure.

A biopsy needle of the character to which the present invention relates is a side cut needle such as that disclosed in U.S. Pat. No. 3,477,423 to Griffith. Such a side cut needle includes a solid stylet telescopically received within an inner tubular cutting cannula which in turn is telescopically received within an outer tubular cannula in which the stylet and inner cannula are supported for axial and rotative displacement relative to one another and to the outer cannula. The stylet is provided with a specimen cutting recess, or tissue receptacle, in the distal portion thereof by which a tissue specimen severed at the biopsy site is removable therefrom. More particularly, the side cut needle is inserted into a patient until the distal end of the outer cannula reaches the lesion where the biopsy specimen is to be taken, and the stylet is then advanced relative to the outer and inner cannulas into the lesion to the biopsy site. The tissue at the site moves into the specimen recess, and the inner cannula is then advanced relative to the outer cannula and over the stylet to cut the tissue into the specimen recess and to cover the recess and thus entrap the specimen therein for removal from the site. Such removal is achieved by retracting the stylet and inner cutting cannula into the outer cannula and then withdrawing the needle from the patient.

Heretofore, the cutting recess in the stylet component of a biopsy needle has been defined by an axially extending bottom wall parallel to the axis of the stylet and axially spaced apart end walls perpendicular to the bottom wall and thus the stylet axis. When the stylet is advanced into the area from which tissue is to be removed, the tissue enters the recess as the stylet advances therethrough and the tissue is severed and captured in the recess by advancement of the inner cutting cannula relative to the stylet. With a recess of the foregoing structure, it is difficult to obtain a desirable quantity of specimen tissue in the cutting recess and, in this respect, it is not uncommon to withdraw a specimen which, from the standpoint of quantity, is only one-half to three-quarters the quantity which would be removed if the cutting recess were completely filled. This deficiency is due at least in part to the difficulty in maintaining stability with respect to the position of the stylet at the biopsy site during advancement of the cutting cannula relative thereto. When the component parts of the biopsy needle are manually manipulated, for example, there is a tendency to advance and/or withdraw the stylet from its initial position at the biopsy site during advancement of the cutting cannula. Both of these movements cause a portion of the specimen initially received in the cutting recess to be displaced therefrom whereby, when severing is completed by advancement of the cutting cannula, the quantity of tissue captured in the recess is less than that which is possible based on the size of the recess. As another example, biopsy needles of the foregoing structure are often operated through the use of a "gun" by which displacement of the component parts of the needle is automated during the biopsy procedure, and there is a recoil action in connection with such automated guns which tends to push the stylet forwardly from its initial position at the biopsy site during advancement of the cutting cannula. As mentioned above, such advancement of the stylet further into the tissue at the biopsy site causes a portion of the tissue in the cutting recess to be displaced therefrom.

It is believed that the tissue loss encountered with a stylet structured and operated as referred to above is the result of the perpendicular disposition of the end walls of the recess relative to the bottom wall thereof. In this respect, as the stylet is advanced or withdrawn relative to the tissue site during advancement of the cutting cannula, the end walls at the opposite ends of the recess move against the tissue specimen and the perpendicular disposition of the walls tends to deflect the tissue laterally outwardly of the recess. Thus, the quantity of tissue which is captured in the recess upon completing the advancement of the cutting cannula is reduced relative to the optimum capability of the recess.

SUMMARY OF THE INVENTION

The present invention provides improvements in the construction of the stylet of a biopsy needle by which the foregoing problems are overcome. More particularly in this respect, the recess of a stylet in accordance with the present invention has a bottom wall parallel to the axis of the stylet and distal and proximal end walls between the bottom wall and the outer surface of the stylet which provide the recess with an entrance end radially spaced from the bottom wall and an inner portion which is axially enlarged relative to the entrance end. This configuration of the recess is achieved by providing for at least one of the distal and proximal end walls, and preferably both, to be reentrant from the entrance end of the recess with respect to the corresponding one of the distal and proximal portions of the stylet, whereby the recess has a portion radially inwardly of the entrance end which has an axial dimension greater than the axial dimension of the entrance end.

With respect to the quantity of specimen tissue which can be captured and removed from a biopsy site with a biopsy needle having a stylet according to the present invention, the reentrant disposition of each of the distal and proximal end walls of the recess provides independent advantages in conjunction with the biopsy procedure and an optimum advantage with regard to the procedure when both end walls are reentrant. With regard to the reentrant disposition of the distal end wall of the recess, the latter provides a notch at the distal end of the recess which functions to secure the stylet in the tissue against withdrawal of the stylet while the cutting cannula is advanced forward to complete the cutting and capturing of the specimen in the stylet recess. Furthermore, the radially outer edge of the end wall is generally of elliptical contour and not in a plane perpendicular to the stylet axis, and thus enhance cutting of the tissue specimen by rotation of the stylet prior to advancement of the cutting cannula. The reentrant disposition of the proximal end Wall of the recess provides a notch which functions to secure the stylet in the tissue against advancement further into the biopsy site from the initial position during advancement of the cutting cannula to complete the cutting and capturing operation. Further, as with the distal end wall, the proximal end wall has an outer edge which can enhance cutting of 647 the tissue specimen.

The notches provided by the reentrant dispositions of the distal and proximal end walls of the recess provide the further advantage of holding the tissue specimen firmly against the cutting recess and against lateral separation therefrom, thus to enhance cutting of the tissue when the cutting cannula is advanced and to optimize the quantity of tissue which is captured and removed from the biopsy site. In this respect, the notch at the proximal end of the recess is driven into the tissue and the reentrant disposition of the proximal end wall pushes the tissue radially inwardly of the recess and into the corner between the proximal end wall and bottom wall of the recess and thus holds the tissue against separation from the recess. The notch at the distal end of the recess enhances filling the axial length of the recess with tissue during the biopsy process in that the reentrant disposition of the distal end wall of the recess also serves to capture tissue in the notch provided thereby thus to hold the tissue against displacement radially outwardly of the recess during advancement of the cutting cannula.

It is accordingly an outstanding object of the present invention to provide a biopsy needle stylet with an improved cutting recess structure.

Another object is the provision of a stylet of the foregoing character in which the cutting recess promotes securing the stylet in the tissue at a biopsy site against axial displacement relative thereto during a biopsy procedure.

A further object is the provision of a stylet of the foregoing character which optimizes the quantity of tissue which can be removed from the biopsy site during the biopsy procedure.

Yet another object is the provision of a stylet of the foregoing character wherein the cutting recess is structured to hold the tissue in place relative to the recess during advancement of a cutting cannula relative thereto to cut and capture the specimen in the recess.

Still a further object is the provision of a stylet of foregoing character in which the cutting recess includes distal and proximal end walls which are reentrant with respect to the distal and proximal portions of the stylet, respectively.

Still another object is the provision of a biopsy needle including an improved stylet of the foregoing character.

BRIEF DESCRIPTION OF THE DRAWINGS

The foregoing objects, and others, will in part be obvious and in part pointed out more fully hereinafter in conjunction with the written description of preferred embodiments of the invention illustrated in the accompanying drawings in which:

FIG. 5 is a sectional side elevation view showing the outer cannula, cutting cannula and stylet of a biopsy needle in accordance with the present invention in assembled relationship prior to use of the needle;

FIGS. 6 and 7 are side elevation views, partially in section, showing the various positions of the component parts of the needle as a biopsy specimen is taken; and FIG. 8 is a side elevation view, partially in section, of another embodiment of a biopsy needle stylet in accordance with the present invention.

DESCRIPTION OF PREFERRED EMBODIMENTS

Figure 1:
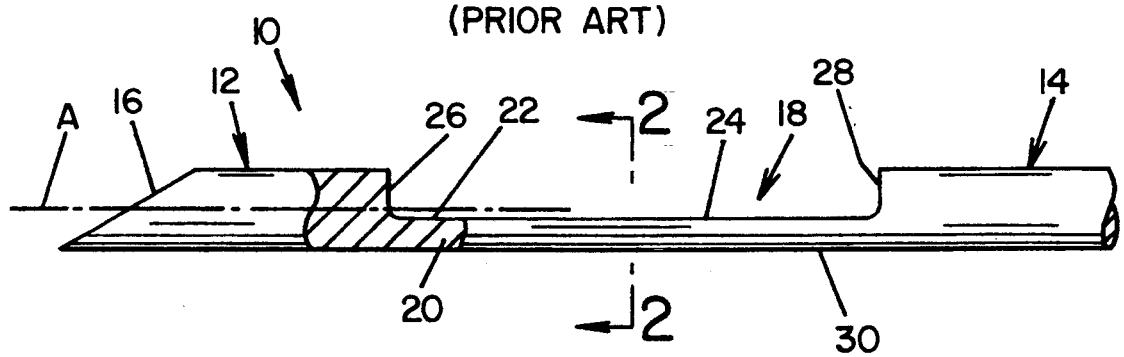
FIG. 1 is an elevation view, partially in section, of a prior art biopsy needle stylet.
Figure 2:
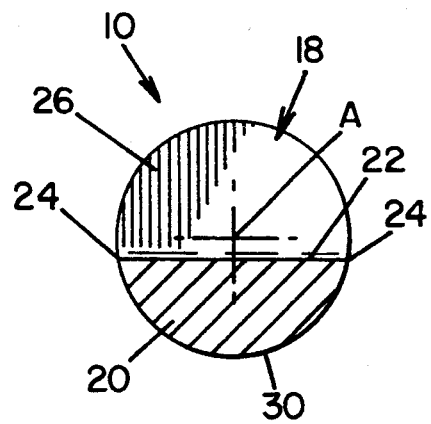
FIG. 2 is a cross-sectional elevation view of the stylet taken along line 2—2 in FIG. 1.

Referring now in greater detail to the drawings, wherein the showings are for the purpose of illustrating preferred embodiments of the invention only and not for the purpose of limiting the invention, FIGS. 1 and 2 illustrate a prior art biopsy needle stylet 10 which is solid and circular in cross-section having an axis A and a diameter which, as is well known, provides for the stylet to be slidably and rotatably received in a tubular inner or cutting cannula of a biopsy needle. Stylet 10 includes a distal portion 12 and a proximal portion 14 extending axially inwardly therefrom, and the axially outer end of distal portion 12 is beveled to provide a distal tip or end 16. The stylet is radially and axially cut away at a location between distal end 16 and proximal portion 14 to provide a specimen receiving recess 18 and a solid portion 20 spanning the recess. Recess 18 includes a bottom wall 22 parallel to axis A and having axially extending laterally opposite edges 24 which provide cutting edges for severing a specimen at the biopsy site if the stylet is rotated. Recess 18 further includes a distal end wall 26 and a proximal end wall 28, each of which extends perpendicular to bottom wall 22 and between the bottom wall and outer surface 30 of the stylet.

Figure 3:
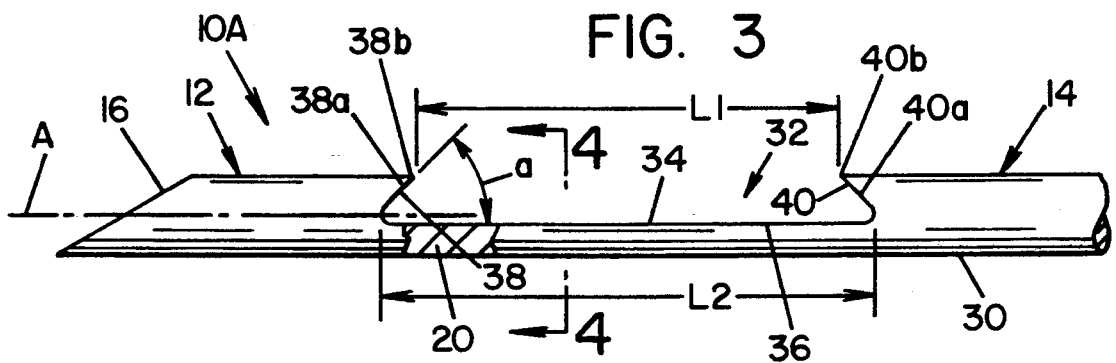
FIG. 3 is a side elevation view, partially in section, of a biopsy needle stylet in accordance with the present invention.
Figure 4:
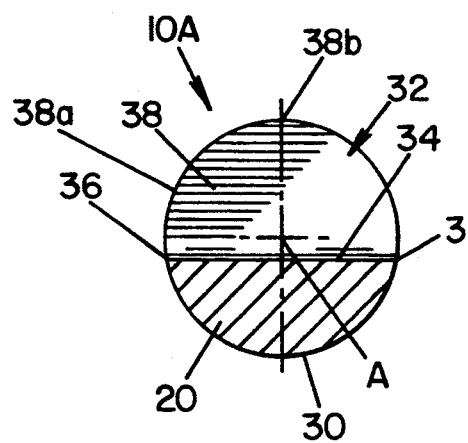
FIG. 4 is a cross-sectional elevation view of the stylet in FIG. 3 taken along line 4—4 therein.

FIGS. 3 and 4 illustrate a modification of the recess in a stylet of the foregoing character to provide a stylet 10A in accordance with the present invention. With the exception of the recess, stylet 10A corresponds to stylet 10 described above, whereby like numerals are used in FIGS. 3 and 4 to designate corresponding parts of the stylet. Referring to the latter figures, stylet 10A is provided with a recess 32 having an axially extending bottom wall 34 parallel to axis A and providing axially extending laterally opposite edges 36 corresponding to edges 24 of stylet 10 in FIGS. 1 and 2. Recess 32 includes a distal end wall 38 and a proximal end wall 40, each of which extends between bottom wall 34 and outer surface 30 of the stylet and each of which, is reentrant with respect to the corresponding one of the distal and proximal portions 12 and 14 of the stylet. The reentrant disposition of walls 38 and 40 provides for recess 32 to have an entrance end radially spaced from bottom wall 34 and having an axial dimension L1, and a portion radially inwardly of the entrance end and having a major axial dimension L2 which is greater than dimension L1. In the embodiment illustrated in FIGS. 3 and 4, walls 38 and 40 are planar, and the reentrant disposition thereof is provided by inclining each of the walls at an acute angle a relative to bottom wall 34. Angle a is between 15° and 85° and, preferable is about 45°. Wall 38 has a radially outer edge 38a which is elliptical in contour when viewed perpendicular to bottom wall 34, and wall 40 has a radially outer edge 40a of the same contour. Edges 38a and 40a intersect an axial plane perpendicular to bottom wall 34 at points 38b and 40b, respectively, to provide dimension L1 for the entrance end of the recess. Further, while the intersections between walls 38 and 40 and the corresponding end of bottom wall 34 are shown as being rounded, it will be appreciated that such intersections could be defined by sharp corners or by rounded corners of larger radius than shown.

Referring now to FIG. 5 of the drawing, stylet 10A is shown in assembled relationship with a tubular inner cutting cannula 42 and a tubular outer cannula 44 to provide a biopsy needle in which the stylet and cannulas are coaxial and supported for relative axial and rotational displacement relative to one another. Inner cutting cannula 42 has a distal portion 46 including tapered distal cutting edge 48 which includes a cutting tip 50 at the distal end of the cutting cannula, and outer cannula 44 has a distal portion 52 including a tapered distal end 54. Inner cannula 42 has a proximal portion 56 and outer cannula 44 has a proximal portion 58 and, while not illustrated, it will be appreciated that the proximal ends of the cannulas and stylet have handles or the like to facilitate manual manipulation of the needle parts relative to one another. Alternatively, the proximal ends have the necessary connections for interengaging the needle parts with a gun by which the operation of the needle is automated.

When assembled, cutting cannula 42 and stylet 10A are displaceable between retracted and extended positions relative to outer cannula 44 and, prior to use, are in the retracted positions thereof shown in FIG. 5. In use, with the inner cannula and stylet in the retracted positions thereof, the needle is inserted into the body of a patient until the distal ends of the component parts of the needle are adjacent a lesion 60 from which a biopsy specimen is to be taken, as shown in FIG. 5. When so positioned, stylet 10A is displaced axially outwardly relative to the outer and inner cannulas from its retracted position to its extended position in which specimen recess 32 is located at the biopsy site in lesion 60 as shown in FIG. 6. As will be appreciated from the latter Figure, the reentrant notched configuration of end walls 38 and 40 relative to bottom wall 34 of recess 32 stabilizes stylet 10A against axial displacement in the lesion and, in response to any such axial displacement, the walls engage and bias the adjacent ends of the tissue in the recess inwardly against bottom wall 34. This advantageously precludes the end portions of the tissue from being displaced outwardly through the entrance into the recess during completion of the specimen cutting operation and which displacement would result in a loss of a quantity of the tissue specimen which would otherwise be captured and removed from the site.

When stylet 10A is located at the biopsy site in lesion 60 as shown in FIG. 6, the stylet can be rotated about axis A as indicated by arrow 62 for one of the edges 36 of bottom wall 34 and edges 38a and 40a of end walls 38 and 40 to sever the tissue at the biopsy site. The reentrant disposition of end walls 38 and 40 of recess 32 provides the further advantage of enhancing cutting of tissue by rotation of stylet 10A relative to the cutting which can be achieved with a stylet in which the end walls of the recess are perpendicular to the bottom wall thereof. In this respect, the reentrant configuration captures the adjacent end portions of the tissue against the bottom wall of the recess as described above, whereby edges 38a and 40a of the end walls are more effective in severing the tissue in response to rotation of the stylet about axis A. In any event, when stylet 10A is at the biopsy site, cutting cannula 42 is displaced axially outwardly relative to outer cannula 44 and stylet 10A from its retracted position shown in FIG. 6 to its extended position shown in FIG. 7. During such movement of cutting cannula 42, cutting edge 48 and tip 50 at the distal end thereof cut the tissue at the biopsy site into recess 32 and, in moving axially across the recess, cannula 42 radially captures a specimen S in recess 32 as shown in FIG. 7. As mentioned hereinabove, the quantity of specimen captured in recess 32 during movement of cutting cannula 42 to the position shown in FIG. 7 is optimized by the stabilizing effect against axial displacement of cannula 10A which is provided by the reentrant configuration of recess walls 38 and 40. When the tissue specimen S has been captured in recess 32 as described above, stylet 10A and cutting cannula 42 are withdrawn together from the lesion to their retracted positions relative to outer cannula 44, as shown in FIG. 5, and the needle is then withdrawn from the patient.

FIG. 8 illustrates another embodiment of a stylet in accordance with the present invention. In this embodiment stylet 10B is identical to stylet 10A described above with the exception of the contour of the end walls of the specimen recess, whereby like numerals are employed in FIG. 8 to designate the parts of stylet 10B corresponding to those of stylet 10A. In this embodiment, cutting recess 32 has distal and proximal end walls 64 and 66, respectively, which are reentrant from outer surface 30 of the stylet with respect to the corresponding one of the distal and proximal portions 12 and 14 of the stylet. End walls 64 and 66 are of an arcuate contour between bottom wall 34 of the recess and outer surface 30 of the stylet and include circumferentially extending radially outer side edges 64a and 66a, respectively. Edges 64a and 66a intersect an axial plane perpendicular to bottom wall 34 at points 64b and 66b, respectively, to provide the recess with an entrance end having an axial dimension L1. The reentrant disposition of end walls 64 and 66 provides for the recess to have a portion radially inwardly of the entrance end having a major axial dimension L2 which is greater than dimension L1. As will be appreciated from the description of stylet 10A hereinabove, the reentrant disposition of end walls 64 and 66 provides for stylet 10B to provide the same functions as end walls 38 and 40 of stylet 10A in connection with use of a biopsy needle including stylet 10B.

While considerable emphasis has been placed herein on the structures of preferred embodiments of the stylets, it will be appreciated that other structures as well as modifications of the disclosed structures can be made without departing from the principles of the invention. In this respect, for example, the end walls of the tissue cutting recess of the stylet can be V-shaped with the apex of the V parallel to the bottom wall of the recess and located between the bottom wall and outer surface of the stylet. Further, the reentrant configurations of the distal and proximal end walls of the recess do not have to be the same and, for example, can include a combination of a planar inclined wall as shown in connection with stylet 10A together with an arcuate wall as shown in connection with stylet 10B. As a further example, the acute angles between the end walls and bottom wall of stylet 10A do not have to be the same. These and other modifications of the preferred embodiments as well as other embodiments of the invention will be obvious and suggested to those skilled in the art, whereby it is to be distinctly understood that the foregoing descriptive matter is to be interpreted merely as illustrative of the invention and not as a limitation.

Having thus described the invention it is claimed:

1. In a biopsy needle for taking a biopsy specimen from a site in a patient comprising an outer tubular cannula having an axis, an inner tubular cannula coaxial with and relatively displaceably received in said outer cannula, and a styler coaxial with and relatively displaceably received in said inner cannula, said stylet having an outer surface, a distal end, a proximal portion and a specimen recess therebetween for receiving a specimen at said site, said recess opening radially into said stylet from said outer surface and having an axially extending bottom wall and axially spaced apart distal and proximal end walls between said bottom wall and said outer surface and providing said recess with an entrance end radially spaced from said bottom wall, the improvement comprising: said entrance end having a first axial dimension, and at least one of said distal and proximal end walls being reentrant from said entrance end of said recess with respect to the corresponding one of said distal end and proximal portion of said stylet, whereby said recess has a second axial dimension radially inwardly of said entrance end greater than said first dimension.

2. A biopsy needle according to claim 1, wherein said at least one wall is inclined at an acute angle relative to said bottom wall.

3. A biopsy needle according to claim 2, wherein said acute angle is about 45°.

4. A biopsy needle according to claim 1, wherein said at least one wall is arcuate between said entrance end and said bottom wall.

5. A biopsy needle according to claim 1, wherein both said distal and said proximal end walls are reentrant from said entrance end.

6. A biopsy needle according to claim 5, wherein each of said distal and proximal end walls is arcuate between said entrance end and said bottom wall.

7. A biopsy needle according to claim 5, wherein each of said distal and proximal end walls is inclined at an acute angle relative to said bottom wall.

8. A biopsy needle according to claim 7, wherein said acute angle is about 45°.

9. A biopsy needle according to claim 1, wherein said entrance end of said recess is at said outer surface of said stylet and said at least one end wall is reentrant from said outer surface.

10. A biopsy needle according to claim 9, wherein both said distal and said proximal end walls are reentrant from said outer surface.

11. A biopsy needle according to claim 10, wherein each said distal and said proximal end wall is arcuate between said outer surface and said bottom wall.

12. A biopsy needle according to claim 10, wherein each said distal and said proximal end wall is planar and inclined at an acute angle with respect to said bottom wall.

13. A biopsy needle according to claim 12, wherein said acute angle is about 45°.

14. A stylet for a biopsy needle, said stylet comprising a metal body portion having an axis, a distal end, a proximal portion axially spaced from said distal end, a circular outer surface between said distal end and said proximal portion, and a specimen recess in said outer surface, said recess including an axially extending bottom wall and distal and proximal end walls between said bottom wall and said outer surface and providing said recess with an entrance end radially spaced from said bottom wall, said entrance end having a first axial dimension and at least one of said distal and said proximal walls being reentrant from said entrance end with respect to the corresponding one of said distal end and proximal end portion of said stylet, whereby said recess has a second axial dimension radially inwardly of said entrance end greater than said first dimension.

15. A stylet according to claim 14, wherein said at least one wall is inclined at an acute angle relative to said bottom wall.

16. A stylet according to claim 14, wherein said acute angle is about 45°.

17. A stylet according to claim 14, wherein said at least one wall is arcuate between said entrance end and said bottom wall.

18. A stylet according to claim 14, wherein both said distal and said proximal end walls are reentrant from said entrance end.

19. A stylet according to claim 18, wherein each of said distal and proximal end walls is arcuate between said entrance end and said bottom wall.

20. A stylet according to claim 18, wherein each of said distal and proximal end walls is inclined at an acute angle relative to said bottom wall.

21. A stylet according to claim 20, wherein said acute angle is about 45°.

22. A stylet according to claim 14, wherein said entrance end of said recess is at said outer surface of said stylet, and both said distal and said proximal end walls are reentrant from said outer surface.

23. A stylet according to claim 22, wherein each said distal and said proximal end wall is arcuate between said outer surface and said bottom wall.

24. A stylet according to claim 22, wherein each said distal and said proximal end wall is planar and inclined at an acute angle with respect to said bottom wall.

25. A stylet according to claim 24, wherein said acute angle is about 45°.

* * * * *